(12) United States Patent
Resnick

(10) Patent No.: US 6,280,379 B1
(45) Date of Patent: Aug. 28, 2001

(54) SPECULUM

(76) Inventor: Scott Resnick, 922 Steele St., Denver, CO (US) 80206

( * ) Notice: Subject to any disclaimer, the term of this patent is extended or adjusted under 35 U.S.C. 154(b) by 0 days.

(21) Appl. No.: 09/728,214

(22) Filed: Dec. 1, 2000

Related U.S. Application Data

(60) Provisional application No. 60/168,578, filed on Dec. 2, 1999.

(51) Int. Cl.[7] .................................................. A61B 17/02
(52) U.S. Cl. ............................................................ 600/220
(58) Field of Search .................................. 600/219, 220, 600/222, 224, 201, 235

(56) References Cited

U.S. PATENT DOCUMENTS

| | | | |
|---|---|---|---|
| 52,014 | * 1/1866 | Bartlett | 600/224 |
| 55,511 | * 6/1866 | Leutz | 600/224 |
| 350,721 | * 10/1886 | Cooper | 600/224 |
| 351,548 | * 10/1886 | Watson | 600/224 |
| 380,745 | * 4/1888 | Chamberlin | 600/224 |
| 2,083,573 | * 6/1937 | Morgan | 600/224 |
| 5,377,667 | 1/1995 | Patton et al. . | |
| 5,505,690 | 4/1996 | Patton et al. . | |
| 5,509,893 | 4/1996 | Pracas . | |
| 6,048,308 | * 4/2000 | Strong | 600/224 |
| 6,174,282 | * 1/2001 | Tan | 600/224 |

* cited by examiner

Primary Examiner—Gene Mancene
Assistant Examiner—Eduardo C. Robert
(74) Attorney, Agent, or Firm—Sheridan Ross P.C.

(57) ABSTRACT

A speculum is provided for examining a body cavity by the use of a one handed, simplistic design which improves visualization, is more comfortable to the patient and which can be manufactured in a cost effective manner.

24 Claims, 5 Drawing Sheets

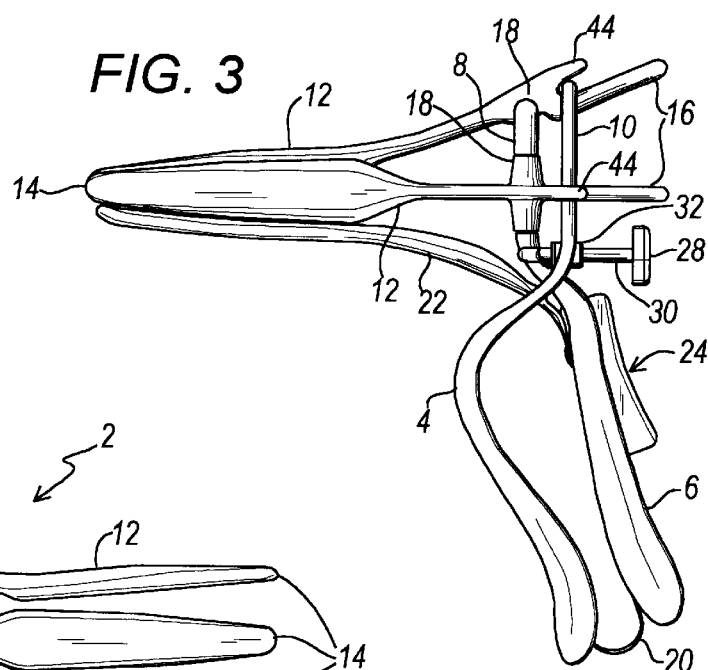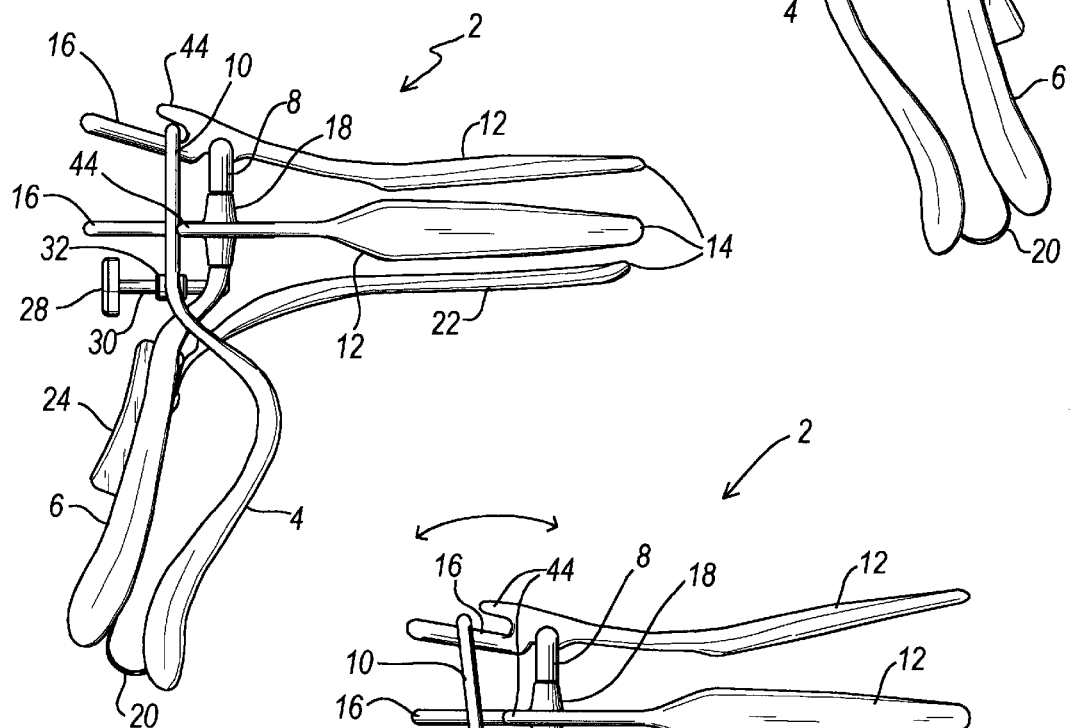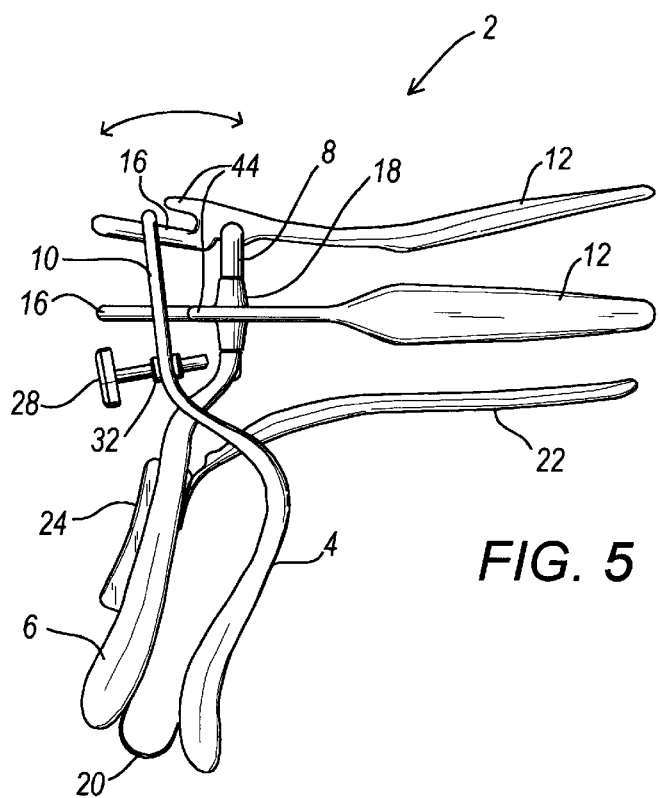

SPECULUM

The present application claims priority of U.S. Provisional Patent Application Serial No. 60/168,578 having a filing date of Dec. 2, 1999, the application being incorporated herein by reference in its entirety.

FIELD OF THE INVENTION

The present invention relates to hand-held medical devices, and more specifically speculums used for examining body cavities.

BACKGROUND OF THE INVENTION

The vaginal speculum is a device which has long been used to visualize the cervix and vaginal walls, as well as to gain trans-cervical access to the uterus. The mechanics of a typical speculum are based on a simple design, one which articulates two "blades" on a handle to expand the vaginal walls in an anterior-posterior, or "front to back" orientation. For years this design has provided adequate exposure and visualization for examining physicians, and allowing for the diagnosis and treatment of vaginal, cervical and endometrial disorders.

Any health care provider familiar with the design and operation of a typical speculum has at one or more times been made aware of its limitations. Most apparently, its basic design is uncomfortable to the patient, and frequently elicits anxiety and apprehension toward the vaginal exam. The prior art speculum design is intended to open the vagina, an oval or 'H' shaped structure, with two metal or plastic "duck-billed" blades which diverge relative to one another. The broad, flattened orientation of the blades does not respect the oval contour of the vaginal vault, and its insertion is often uncomfortable or painful to the patient. In addition, the broad anterior blade is subject to compress the patient's urethrae as it courses beneath the pubic bone. This is an uncomfortable situation for the healthy patient and often a desperate one for the patient with a bladder or urethra complication. Common complaints additionally include the sensation of a cold metal tool being placed in the vagina, or simply the difficulties met with its insertion.

From the health care provider's perspective, the tool's objective of providing visualization of the cervix is far from optimal. As the blades may only be opened in a single anterior-posterior plane, there is no support for the lateral "windows" which form as the blades move away from one another. This permits the redundant, fatty and poorly supported tissue on the vaginal sidewalls to bulge inward as the blades are opened, invariably obscuring a portion of, if not the entire cervical margins. This phenomenon is almost the rule, not the exception, in obese or multiparous patients.

A vicious cycle then ensues with the prior art design. As the vaginal sidewalls collapse inward, the practitioner attempts to improve visualization by opening the tool wider in the hope of stretching the redundant tissue to a point at which they can no longer collapse. This naturally causes great discomfort for the patient and frustration for the care provider. A technique of placing a condom over the blades and cutting a hole in the tip has been used widely to improve visualization, while other physicians have opted for the expense and inconvenience of using lateral wall retractors in the vagina to supplement the speculum. The former method is sub-adequate as it severely limits visualization, mobility and speculum expansion. The latter method is impractical, expensive, and crowds two tools into an already limited work space. Further, since the typical speculum is only applicable in a minimum number of sizes without interchangeable blades, it is not readily adapted to be used with a variety of different patients and anatomies associated therewith.

Conventional speculum designs not only limit visualization of the cervix, but frequently induces tissue trauma. As the two blades are positioned and opened, the top blade is opened and dragged across the cervix. With a frequent and uncomfortable "pop" the cervix is scraped along the anterior blade as it comes into view. With friable or inflamed tissue this immediately causes bleeding and pain, further compromising the exam. Thus, the cervix and vagina are often poorly visualized and sampled, compromising the screening, diagnosis, and treatment of genital pathology.

One attempt to design a more efficient and patient friendly speculum is described in U.S. Pat. Nos. 5,505,690 and 5,377,667 to Patton. The device disclosed in these patents utilizes a plurality of plastic blades pivotally interconnected to a base. The blades have distal ends which move outwardly when the handle is depressed. The outward movement is accomplished by a traveling ring being pushed forward in a linear direction with an actuator and the base which is interconnected to the rearward handle. Unfortunately, the device is difficult to open based on the mechanics of the opening mechanism, has blade tips which are too large, thus causing pain and discomfort in many patients. Further, the Examining "window" is inherently small due to the design and the handle is inconveniently located directly behind the longitudinal axis of the blades.

Thus, with the aforementioned limitations in mind, an improved speculum design would be extremely advantageous which offers increased patient comfort, improved visualization and greater adaptability for the care provider.

SUMMARY OF THE INVENTION

It is thus an object of the present invention to provide a speculum which provides greater patient comfort, is easier to use by the health care provider, can be modified for different sizes of body cavities, is simplistic in design and can be manufactured at a reasonable cost.

Thus in one aspect of the present invention, a speculum is provided which has improved visualization for the attending physician based on the position of the handle and examination "window" as seen through a stationary ring. As the handle is squeezed, a radial expansion of the speculum's arms allows for lateral retraction of the vaginal walls with each examination. Decreased mass through the arms of the speculum confers greater visualization of the vaginal sidewalls, and the contoured, rounded shape permits easier rotation of the tool within the vagina.

It is a further aspect of the present invention to provide a speculum which improves patient comfort and reduces the anxiety and fear often associated with an exam. Thus, a more ergonomic design is provided permits an easier, more natural and more comfortable insertion. This is accomplished by using a "bullet shaped", small diameter tip on the distal ends of the blades. Further, the blades may be comprised of plastic, or coated to reduce friction or the cold sensation associated with metallic tools. Further, with a "four-point" basis of vaginal wall expansion rather than the traditional "two", i.e., four blades as opposed to two, less blade material is needed to expand the vaginal walls which provides even greater visualization and a less traumatic exam. Lastly, by circumventing the vaginal wall's inherent desire to collapse inward between the opened blades, less force and subsequently less discomfort is required to obtain the required visualization.

It is yet another aspect of the present invention to provide a vaginal speculum which has interchangeable parts. Since not all vaginas are the same shape, and not all cervixes are directed axially down the vaginal tube, a speculum is needed which can be adapted to fit the patient, as opposed to every patent having to adapt to a consistent size and shaped speculum. The improved speculum provided herein allows for the simple and expedient exchange of any or all of the interchangeable blades. This provides several advantages. First it allows the tool to be tailored to fit vaginas with an irregular axis or loss of the "normal" anatomical orientations due to scarring, intra-abdominal adhesions, or previous surgery. In addition, should a modification of the tool be needed during the course of the examination, an entirely new speculum need not be contaminated. Replacement of one to three of the blades may be simply exchanged, saving time, parts and sterilization costs.

Further, interchangeable blades provided with the present design offer an advantage to those medical offices which only perform a few examinations a day. The standard housing could be purchased with a variety of interchangeable blades. This would provide for a variety of exam options without the cost of several different examining tools.

By providing a standard housing with easily detachable blades, improved sterilization is realized. The ability to easily disarticulate the tool decreases the potential spaces, notably hinges and screw threads, in which bacteria and viruses could conceivably collect and evade destruction during the sterilization process. In addition, the speculum has a more fluid, graceful and artistic design which is more appealing to both the care providers and patients. Further, the speculum offers complete removal and exchange of the sliding posterior blade, which by design does not move outwardly as the handle is squeezed. This, along with unlimited excursion of the blade along the handle permits infinite options for the posterior exam.

It is a further aspect of the present invention to provide a tool which allows for one-handed operation. Unlike the conventional speculum design which necessitates two hands for expanding and securing the speculum in the "open" position, the new design only requires one, since the opened arms can be locked into position once the arms are expanded. This frees the other hand for instrumentation or manipulation of the operative field and equipment.

It is yet another aspect of the present invention to provide a speculum with an optional smoke evacuator and fiber-optics light source. Blades with built-in smoke evacuators as well as fiber-optic light sources will improve visualization and safety for electrosurgical procedures. These components can be easily and quickly added to one or more blades in different positions as the clinical situation dictates.

Finally, it is a further aspect of the present invention to provide a speculum with radially expanding rings, and non-linear shaped blades. By opening the divergent stationary and traveling rings along an arc, the moveable pivot blades enact a greater amount of travel at its tip than its lateral counterparts, as the traveling ring traverses further along the fulcrum.

This permits the primary amount of opening along the anterior-posterior axis, with the lateral blades serving as supplemental sidewall retraction.

Thus, in one aspect of the present invention, a speculum is provided herein and comprising:

a handle having a rearward portion and a forward portion;
a biasing means interconnected to said handle which maintains said rearward portion and said forward portion of said handle in a spaced apart relationship;
a stationary ring interconnected to an upper portion of said rearward portion of said handle;
a traveling ring interconnected to said forward portion of said handle and positioned behind said stationary ring;
a plurality of blades having a front end and a rear end and a pivot point positioned therebetween which is pivotably engaged to said stationary ring, said rear end of said plurality of blades positioned at least partially within an interior diameter of said traveling ring, wherein when said handle is squeezed, said traveling ring travels away from said stationary ring, wherein said plurality of said blades pivot around said stationary ring, and said front ends of said plurality of blades are separated.

BRIEF DESCRIPTION OF THE DRAWINGS

FIG. 3 is a left elevation view of the speculum shown in FIG. 1 with the pivoting blades and traveling blade shown in a closed position;

FIG. 4 is a right elevation view of the present invention and showing the traveling blades and sliding blade in a partially opened position;

FIG. 5 is a right elevation view of the speculum shown in FIG. 1 with the traveling blade and pivoting blades in a fully opened position;

DETAILED DESCRIPTION

Figure 2:
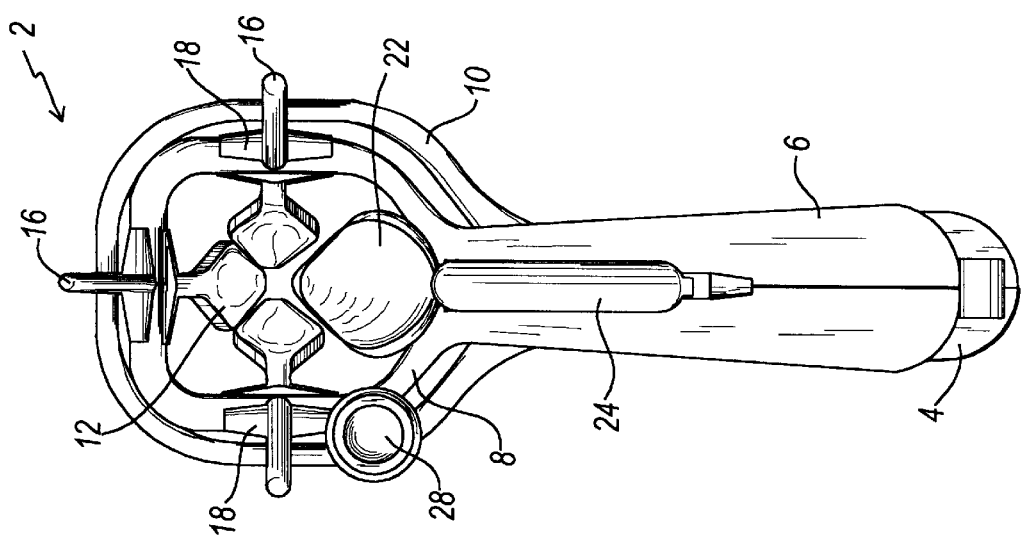
FIG. 2 is a rear elevation view of the speculum of FIG. 1, and identifying the examining window and plurality of pivoting blades.
Figure 1:
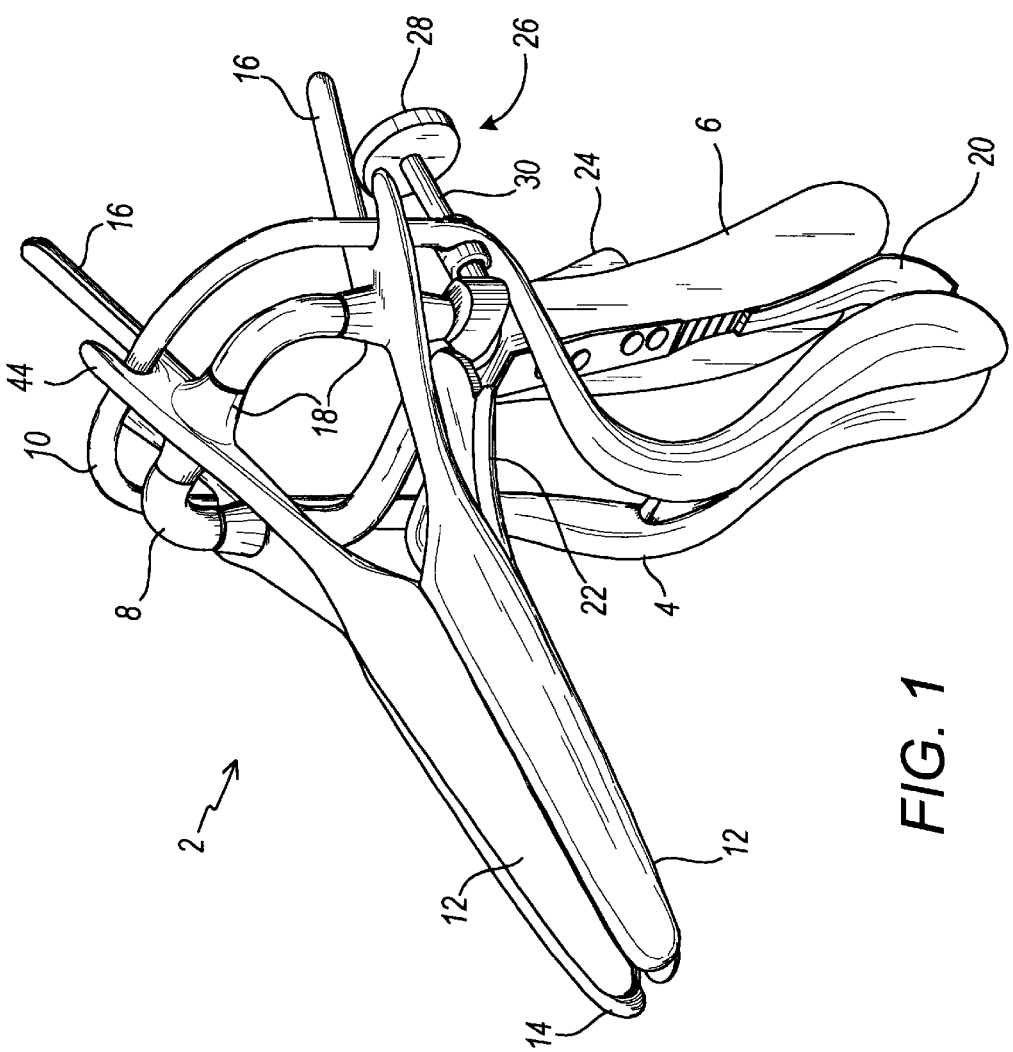
FIG. 1 is a front left perspective view of the present invention.

Referring now to the drawings, FIG. 1 is a left perspective view of the speculum 2 of the present invention. FIG. 2 is a rear elevation view, while FIG. 3 is a left elevation view of the speculum 2 shown in FIG. 1. In general, the speculum 2 is comprised of a forward handle 4 which is interconnected to a rearward handle 6 with a biasing spring 20. The biasing spring serves to keep the forward handle 4 and rearward handle 6 in a spaced apart relationship when not in use. In this position of non-use, the front ends 14 of the blades 12 are oriented in a closed position. On the upper end of the forward handle 4 is a traveling ring 10 which serves to open a plurality of pivoting blades 12 as will be discussed in greater detail below. The rearward handle 6 is interconnected to a stationary ring 8 on the upper portion which serves to support the plurality of pivoting blades 12.

The pivoting blades 12 generally have a front end 14, a hook end 16 and a blade sleeve 18 positioned therebetween. A tail 44 is also positioned between the blade sleeve 18 and hook end 16 for engagement with the traveling ring 10 when pressure is removed from the handle. The blade sleeve 18 is used to pivotally interconnect the pivoting blades 12 to the stationary ring 8. By creating a close tolerance between the internal diameter of the pivoting blade sleeve 18 and an outer diameter of the stationary ring 8, the pivoting blades 12 may be selectively removed for sterilization purposes, or to interconnect smaller or larger blades dependent on the needs of the patient and the attending physician. The pivoting blade hook end 16 is designed to be in operable engagement with the traveling ring 10, which again is interconnected to an upper portion of the forward handle 4. As seen in FIGS. 1–3, the blade hook end 16 is not permanently interconnected to the traveling ring I 0 to facilitate quick and easy removal of the pivoting blade 12 as necessary.

Positioned below the plurality of pivoting blades 12 is a sliding blade 22 which is slidingly engaged to the rearward handle 6. By the use of a sliding blade ratchet assembly 24 or other means commonly known in the art, the sliding blade 22 may be selectively moved in a vertical direction with respect to the plurality of pivoting blades 12. Thus, the sliding blade 22 does not move outwardly with respect to the pivoting blades 12 when the forward handle 4 is squeezed with respect to the rearward handle 6.

As additionally seen in FIGS. 1–3, a locking assembly 26 may be provided to maintain the speculum 2 in an open position during use. More specifically, when the forward handle 4 and rearward handle 6 are squeezed, the traveling ring 10 moves away from the stationary ring 8 which in turn provides a force on the blade hook end 16 which moves the blade front end 14 outward. When the blade front end 14 is opened for examination purposes, it is often beneficial for an attending physician to have one hand free for examination purposes or to use other instruments. To facilitate one handed use, the locking assembly 26 may be implemented by turning the head 28 in a clockwise direction which is threadingly engaged with a shaft 30 to a threaded sleeve 32, which is in turn interconnected to the traveling ring 10. When the speculum 2 is in an open position, the head 28 is simply turned to engage the shaft 30 of the locking assembly 26 with the stationary ring 8 to keep the speculum in an open position. When it is desired to close the speculum 2, the head 28 is turned in a counterclockwise position to gradually bring the traveling ring and stationary ring 8 in a position proximate one another which in turn brings the pivoting blades 12 back together.

As additionally seen in FIG. 2, the sight "window" provided to the physician is significantly improved over typical speculums as the pivoting blades 12 are expanded. The sight window is defined herein as the minimum diameter of the traveling or stationary ring positioned in front of the pivoting blades 12. Preferably, and as provided herein with the present invention, the sight window is at least about 1.75 inches and preferably 2.0 inches. This dimension represents the internal diameter of the stationary ring 8, which provides a very wide field of view for the physician.

Referring now to FIG. 4, a right elevation view of the speculum shown in FIG. 1 is provided herein. In this drawing, the speculum is shown in a partially opened position. Further, it is apparent that the pivoting blades 12 have been moved apart from one another as the forward handle 4 and rearward handle 6 are squeezed together. In operation, as the handles are squeezed together, pressure is applied to the blade hook end 16 of the pivoting blades 12, which makes each of the plurality of pivoting blades 12 rotate about the stationary ring 8 at the point of interconnection at the blade sleeve 18. Thus, the closer the forward handle 4 and rearward handle 6 are brought together, the further the traveling ring 10 travels away from the stationary ring 8, thus applying an inward force on the pivoting blade hook ends 16.

Referring now to FIG. 5, the speculum 2 can be seen in a fully opened position with the forward handle 4 and rearward handle 6 in proximate relationship thereto. As seen in this drawing, when the traveling ring 10 is positioned at the rearward end of the blade hook end 16, the resulting force opens the pivoting blade front ends 14 to a maximum open position. This is a results of the geometry of the pivoting blades, in combination with the arcuate travel of the stationary ring 8 with respect to the traveling ring 10. Thus, the traveling ring 10 and stationary ring 8 do not move in a strictly linear fashion with respect to one another due to the geometry of the forward handle 4, rearward handle 6, and the biasing spring 20 which interconnects these components near the bottom interior edges.

As appreciated by one skilled in the art, by varying the shape and angle of the pivoting blades 12, including the hook ends and tail 44, as well as the geometric configuration of the forward handle 4 and rearward handle 6, the degree of opening and relevant movement of the pivoting blades 12 can be modified as necessary for the required medical application.

Further, the shape of the pivoting blades 12 has a non-linear, arcuate shape which deflects outwardly as the blades approach the stationary ring 8. This pronounced bend or scalloped shape substantially reduces pressure being applied to the patient's bladder, and allows the blade ends 14 to be opened to a greater degree after insertion in the vagina without causing significant pain to the patient. The deflection and angle ø of the pivoting blades 12 can be seen in FIGS. 4 and 6, and is preferable between about 140° and 170°. Further, the angle of deflection of the pivoting blades 12 can be easily modified if necessary during manufacturing to facilitate the medical procedure or application.

As additionally seen in FIG. 5, the sliding blade 22 has been moved downward from the plurality of pivoting blades 12 by use of a sliding blade rachet assembly 24. The rachet assembly generally permits the attending physician to move the sliding blade 22 in an upward and downward direction relative to the pivoting blades 12 by applying thumb pressure to the sliding blade rachet assembly 24. The sliding blade rachet assembly 24 is generally comprised of a spring biased rachet mechanism which when depressed allows the sliding blade 22 to move and when pressure is released to lock the sliding blade 22 in place with a plurality of ratcheting teeth 40. In a preferred embodiment the ratcheting teeth 40 are integrally formed in the rearward handle 6. Alternatively, a separate racheting mechanism may be constructed and attached to the rearward handle 6. As appreciated by one skilled in the art, the sliding blade rachet assembly 24 may be substituted with many other types of hardware such as screw and wing nut assembly, or other mechanisms which preferably can be operated with one hand for convenience purposes.

Figure 6:
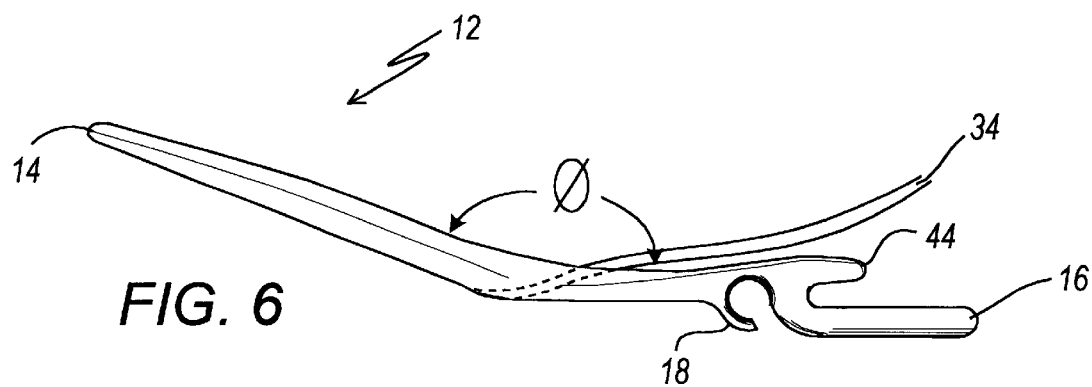
FIG. 6 is a front elevation view of one of the pivoting blades and further identifying a smoke evacuation smoke tube or light tube attachment which is interconnected thereto.
Figure 7:
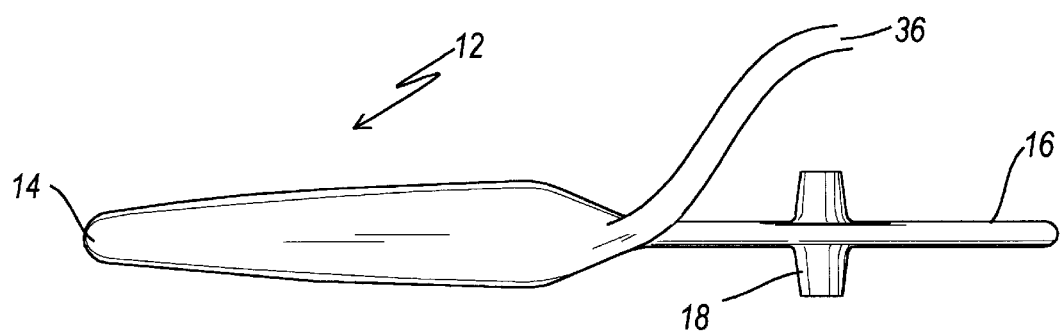
FIG. 7 is a top plan view of the pivoting blade shown in FIG. 6, and further identifying a smoke evacuation tube or light tube interconnected thereto.

Referring now to FIGS. 6 and 7, a front elevation view and a top plan view of an alternative type of a pivoting blade 12 is provided herein. In this particular diagram, a smoke tube 34 and/or a light tube 36, is provided to facilitate removing smoke from the vagina during surgical procedures. The light tube facilitates a fiber optic light or other light means to provide improved visualization for the physician. Preferably, the smoke tube 34 and/or light tube 36 extends along a longitudinal axis of the pivoting blade 12 and terminates on an interior surface of the pivoting blade 12 in a non-obstructing position to maintain an open viewing window. The smoke tube 34 and/or light tube 36 is designed to be used on one or more blades, and may be used in various combinations as necessary.

Figure 8:
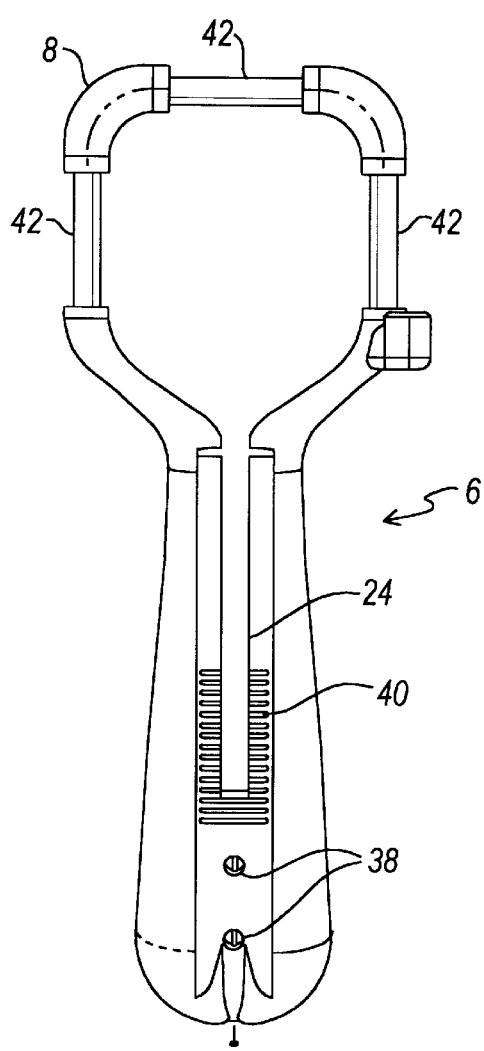
FIG. 8 is a front elevation view of the rearward handle.
Figure 9:
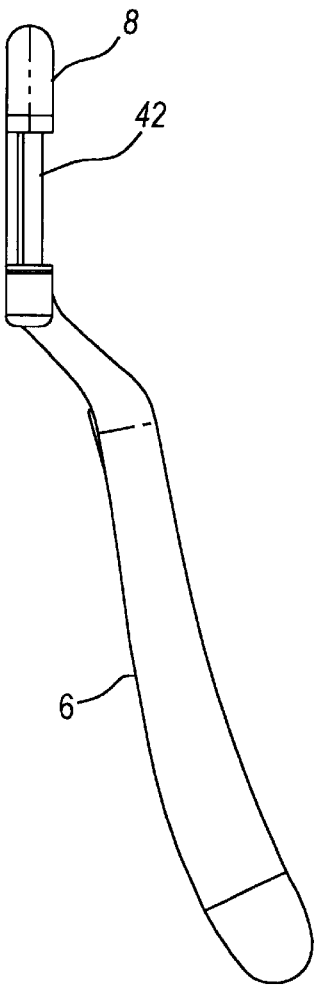
FIG. 9 is a left elevation view of the rearward handle shown in FIG. 8.
Figure 10:
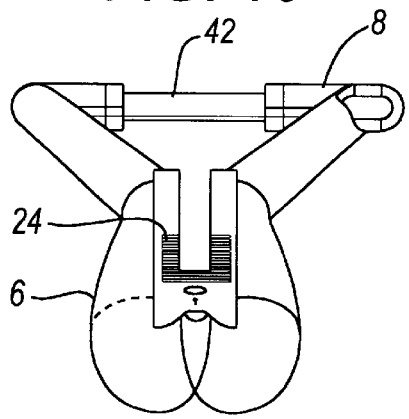
FIG. 10 is a bottom perspective view of the rearward handle shown in FIG. 8.

Referring now to FIGS. 8–10, a front elevation view, left elevation view and a bottom perspective view, respectively are shown of the rearward handle 6 and associated stationary ring 8. As shown in FIG. 8, additional detail of the ratcheting assembly 24 is provided, and which additionally shows the attachment hardware 38 such as screws or rivets, which are used to interconnect the biasing spring 20 to the interior surface of the rearward handle 6 and forward handle 4. As additionally seen in FIG. 8, the diameter of the stationary ring 8 varies from the diameter of the pivot housing 42, which is designed to matingly engage the blade sleeve 18. Further, and as clearly seen in FIGS. 1–3, the traveling ring 10 has a larger diameter than the stationary ring 8. This size difference creates a moment arm around the pivot housing 42 and additionally forces the blade ends 14 to close as the traveling ring 10 engages the blade tail 44.

Figure 11:
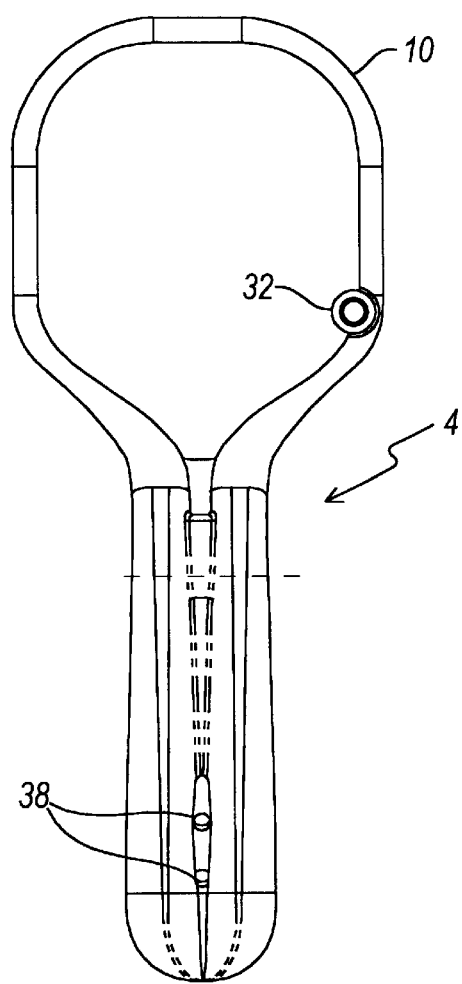
FIG. 11 is a front elevation view of the forward handle and traveling ring assembly.
Figure 12:
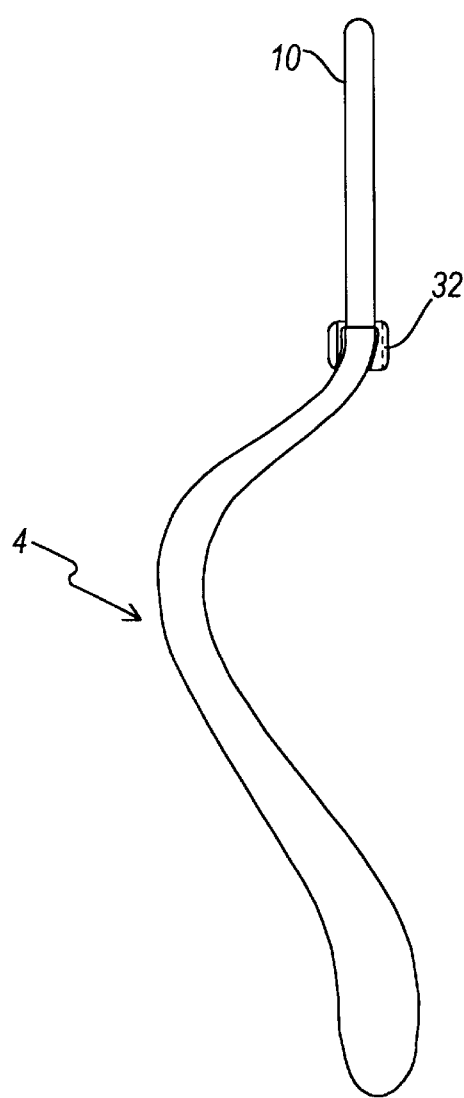
FIG. 12 is a left elevation view of the forward handle and traveling ring assembly shown in FIG. 11.
Figure 13:
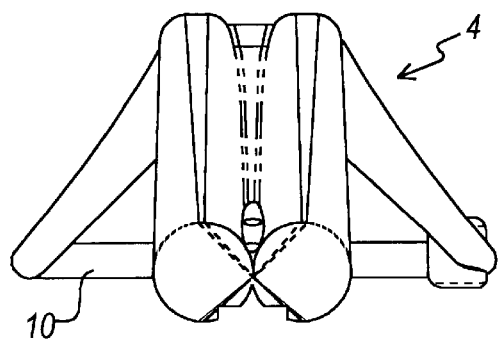
FIG. 13 is a bottom perspective view of the forward handle and traveling ring assembly shown in FIG. 1 1.

Referring now to FIG. 11–13, a front elevation view, side elevation view and rear 10 perspective view, respectively is shown of the forward handle 4 and associated traveling ring 10. Further, the threaded sleeve 32 is shown which in one embodiment is integrally interconnected to the traveling ring 10, and which provides threading engagement for the locking assembly shaft 30. Although the threaded sleeve 32 is shown positioned on the left-hand side, it can also be attached on the right-hand side to facilitate convenience.

Figure 14:
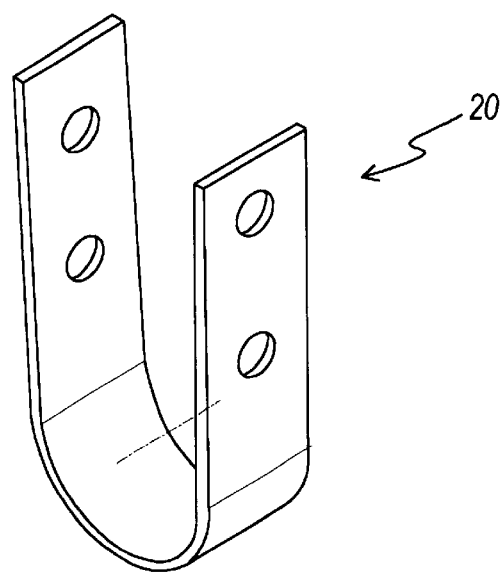
FIG. 14 is a front elevation view of one embodiment of the biasing spring used to interconnect the forward handle and rearward handle.

Referring now to FIG. 14, a typical embodiment of the biasing spring 20 is shown herein. The biasing spring 20 is used to pivotally interconnect the forward handle 4 and the rearward handle 6 as shown in FIG. 1. Preferably, the biasing spring 20 is comprised of a metallic material such as stainless steel, although other materials such as bendable plastics and/or fiberglass or other materials commonly known in the art may be used for the same purpose.

The speculum 2 and associated pivoting blades 12 and sliding blade 22 are preferably comprised of a metallic material such as stainless steel to facilitate sterilization after use. Alternatively, the pivoting blades 12 and sliding blade 22 may be comprised of plastic materials and/or preferably see through plastic materials to improve the comfort of the patient and facilitate better viewing for the examining physician. The pivoting blades and sliding blade 22 may additionally be made of disposable materials to alleviate the time and expense of sterilization. Other materials commonly known in the medical arts such as various rubbers, polyethylene, polypropylene and other materials may additionally be used, as well as rubber and plastic coatings on top of metallic materials. However, non-conductive materials which can be used during electrosurgical procedures are preferred.

The operation and mechanics of the speculum is generally described herein. A forward handle 4 is provided which allows the traveling ring 10 to be withdrawn relative to the rearward handle 6, which allows the stationary ring to travel in a controlled fashion. Once the traveling ring 10 is withdrawn and the speculum 2 is opened, a simple flip of the thumb causes the head 28 of the locking assembly 26 to rotate the shaft 30 within the threaded sleeve 32. This motion directs the shaft 30 forward to apply a force on the back side of the stationary ring 8, resisting the speculum's tendency to return to the resting position with the elastic recoil of the vagina. A simple spin in the opposite direction frees the traveling ring to return to the resting position.

A detachable inferior sliding blade 22 is provided which slides up and down along the rearward handle 6 to permit inferior, or posterior, expansion of the vagina. The interim sliding blade 22 is interconnected in a preferred embodiment with a sliding blade rachet assembly 24 which permits the sliding blade 22 to be moved in a variety of different positions dependent on the patient and medical condition.

Additionally, interchangeable blades of varying lengths may be quickly interconnected to the stationary ring 8 in any variety of combinations. These blades have two points of articulation. The first is the blade sleeve 18, creating a secure fulcrum so that a lever effected moment of the traveling ring 10 along the sloping blade hook ends 16 of the pivoting blades 12 causes the blade front ends 14 to be withdrawn radially, or tangentially from one another. Simple lever mechanics dictates that only a few millimeters of travel must be enacted through the blade hook ends 16 to effect a far greater amount of travel at the blade front ends 14, which rests several centimeters from the point of rotation at the blade sleeve 18. A simple system of articulation with the blade sleeve 18 allows the blades to be positioned and removed with ease. Once snapped into place with either a lock and key fixture, or alternatively a "press-fit" arrangement as shown in the drawings, the locking mechanism will keep the blades 12 from inadvertently falling off the pivot housing 42 of the statutory ring 8. The natural recoil of the biasing spring 20 of the handle returns the traveling ring 10 to its relaxed state, and holding the pivoting blades 12 securely in place. As additionally seen in the drawings, the pivoting blade hook ends 16 additionally have a blade tail 44 which is designed to engage the traveling ring 10 as the traveling ring 10 travels toward the stationary ring 8. Upon engagement, the force of the traveling ring 10 upon the blade tail 44 pushes the pivoting blades 12 together at the distal end.

In an alterative embodiment not shown in the drawings, the second point of attachment of the pivoting blades 12 is with one another. A tongue-in-groove of the sliding blade 22 may allow the two pivoting blades 12 to be seated within these grooves to provide a smaller diameter distal end of the blades. Since the sliding blade 22 ascribes approximately 120° of an arc, this plus the approximately 80° contained in each of the three interchangeable blades 12 will together form a circular apparatus. This arrangement roughly creates a cylinder or tube, permitting a more ergonomic placement into the vagina. The three pivoting blades 12 may be positioned on any of the three pivot housings 42 situated on the stationary ring 8. The two defined points of contact are conserved throughout all possible arrangements of blades. Should one to three longer or shorter blades be necessitated to optimize an exam, they can be easily replaced regardless of the preexisting arrangement, as all blades, regardless of ultimate length, articulate in the same two places.

Alternatively, and as previously discussed, a smoke evacuator tube 34 and fiber-optics tube 36 may be provided. These attachments will be available to optimize the visualization and safety of electrosurgical procedures. A special interchangeable blade will be modeled to accept a vacuum device to remove smoke and potential aerosolized pathogens from the operative field during procedures. Another optional blade will provide a conduit or tube for a small fiberoptic light with an external power source as seen in FIGS. 6 and 7, although the exact positioning of either the fiber optic light source or smoke evacuation tube may vary dictated by the medical procedure and as appreciated by one skilled in the art.

Thus, the present invention provides a speculum with improved visualization, one handed operation, interchangeable blades, an ergonomic design and the option of having smoke evacuator and fiberoptic light accessories. Additionally, the speculum provides an ergonomic design which is more efficient for the care giver and enhances the comfort level of the patient.

For clarity purposes, the following list of components and associated numbering is provided herein:

| No. | Component |
|-----|-----------|
| 2   | Speculum |
| 4   | Forward handle |
| 6   | Rearward handle |
| 8   | Stationary ring |
| 10  | Traveling ring |
| 12  | Pivoting blades |
| 14  | Blade front end |
| 16  | Blade hook end |
| 18  | Blade sleeve |
| 20  | Biasing spring |
| 22  | Sliding blade |
| 24  | Sliding blade ratchet assembly |
| 26  | Locking assembly |
| 28  | Head |
| 30  | Shaft |
| 32  | Threaded sleeve |
| 34  | Smoke tube |
| 36  | Light tube |
| 38  | Assembly hardware |
| 40  | Ratcheting teeth |
| 42  | Pivot housing |
| 44  | Pivoting blade tail |

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described herein above are further intended to explain best modes known in practicing the invention and to enable others skilled in the art to utilize the invention in such, or other embodiments with various modifications required by the particular application(s) or use(s) of the present invention. It is intended the appended claims be construed to include alternative embodiments to the extent permitted by the prior art.

What is claimed is:

1. A speculum adapted for examining a body cavity, comprising:
    a handle having a rearward portion and a forward portion;
    a biasing means interconnected to said handle which maintains said rearward portion and said forward portion of said handle in a spaced apart relationship;
    a stationary ring interconnected to an upper portion of said rearward portion of said handle;
    a traveling ring interconnected to an upper portion of said forward portion of said handle and positioned behind said stationary ring;
    a plurality of blades having a front end and a rear end and a pivot point positioned therebetween which is pivotably engaged to said stationary ring, said rear end of said plurality of blades positioned at least partially within an interior diameter of said traveling ring, wherein when said handle is squeezed, said traveling ring travels away from said stationary ring, and said plurality of said blades pivot around said stationary ring, wherein said front ends of said plurality of blades are separated.

2. The speculum of claim 1, further comprising a sliding blade having a front end and a rear end, said rear end slidingly engaged to said rearward portion of said handle and not in operable contract with said traveling ring.

3. The speculum of claim 2, further comprising adjustment means for selectively positioning said sliding blade on said rearward portion of said handle, wherein the distance between said plurality of blades and said sliding blade is adjustable.

4. The speculum of claim 3, wherein said adjustment means comprises a biased ratcheting mechanism wherein when said ratcheting mechanism is depressed, said sliding blade can travel upward and downward with respect to a longitudinal axis of said plurality of blades.

5. The speculum of claim 1, further comprising locking means interconnected to said traveling ring, wherein said stationary ring and said traveling ring can be selectively maintained in a spaced apart relationship to keep said front end of said plurality of blades spaced apart from one another.

6. The speculum of claim 5, wherein said locking means comprises a head interconnected to a threaded shaft, said shaft received into a threaded housing interconnected to said traveling ring.

7. The speculum of claim 1, wherein said plurality of blades are removably interconnected to said stationary ring, wherein different sizes or types of blades may be selectively interchanged with said speculum.

8. The speculum of claim 1, wherein said biasing means comprises a u-shaped metallic band having a first end interconnected to said rearward portion of said handle and a second end interconnected to said forward portion of said handle.

9. The speculum of claim 1, wherein said plurality of blades are comprised of plastic.

10. The speculum of claim 1, wherein said plurality of blades are comprised of a transparent material.

11. The speculum of claim 1, wherein said front ends of said plurality of blades travel at least about 0.75 inches when said handle is squeezed.

12. The speculum of claim 1, wherein said pivot point of said blades comprises a sleeve which matingly interconnects to said stationary ring.

13. The speculum of claim 1, wherein said traveling ring travels in an arcuate path opposite said stationary ring when said handle is squeezed.

14. The speculum of claim 1, wherein a sight window defined by an internal diameter of said stationary ring is at least about 1.5 inches.

15. The speculum of claim 1, wherein said plurality of blades have a non-linear shape along a longitudinal axis.

16. A handheld apparatus adapted for examining a body cavity, comprising:
    a handle having a rearward portion pivotally interconnected to a forward portion;
    a biasing means operably interconnected to said forward portion and said rearward portion of said handle to maintain said handle in a spaced apart relationship until said handle is squeezed;

a stationary ring interconnected to said rearward portion of said handle and extending upwardly therefrom;

a traveling ring interconnected to said forward portion of said handle and positioned behind said stationary ring;

a plurality of blades each having a first end, a second hooked end and a sleeve positioned therebetween for pivotally engaging said sleeve to said stationary ring, wherein when said handle is squeezed, said traveling ring travels arcuately away from said stationary ring and engages said second hooked ends of said plurality of blades, wherein said first ends of said plurality of blades open with respect to one another.

17. The apparatus of claim 16, further comprising a sliding blade interconnected to a rearward portion of said handle.

18. The apparatus of claim 17, further comprising a sliding blade adjustment means interconnected to said rearward portion of said handle, wherein said sliding blade is selectively adjustable for positioning with respect to said plurality of blades.

19. The apparatus of claim 16, further comprising a locking means interconnected to said traveling ring, wherein said stationary ring and said traveling ring can be selectively positioned in a spaced-apart relationship.

20. The apparatus of claim 16, wherein said plurality of blades are removably attached to said stationary ring.

21. The apparatus of claim 16, wherein said first ends of said plurality of blades have a rounded edge.

22. The apparatus of claim 16, wherein the total diameter of said plurality of blades and sliding blade at a distal end is no greater than about 0.5 inches.

23. A speculum adapted for examining a body cavity, comprising:

a forward handle portion having an upper end and a lower end;

a rearward handle portion having an upper end and a lower end;

a biasing spring interconnecting said forward handle and said rearward handle, wherein said forward handle and rearward handle are biased in a spaced-apart relationship;

a stationary ring interconnected to said upper portion of said rearward handle;

a traveling ring interconnected to said upper portion of said forward handle;

a sliding blade slidingly interconnected to said rearward handle, wherein said sliding blade can be adjusted in a vertical direction; and a plurality of pivoting blades having a first end, a second hook end, and a sleeve positioned therebetween, said sleeve rotatably interconnected to said stationary ring and said second hook ends in operable engagement with said traveling ring, wherein when said forward handle and said rearward handle are squeezed together, said traveling ring travels away form said stationary ring in an arcuate path, engaging said second hooks ends of said plurality of pivoting blades and separating said first ends of said plurality of pivoting blades.

24. The speculum of claim 23, further comprising a threaded sleeve interconnected to said traveling ring for receiving a threaded shaft, wherein when said shaft is extended through said threaded sleeve said traveling ring and said stationary ring can be locked in a spaced-apart relationship.

* * * * *